US005801285A

United States Patent [19]
Waldmann et al.

[11] Patent Number: 5,801,285
[45] Date of Patent: Sep. 1, 1998

[54] PROCESS FOR THE PREPARATION OF 2-METHYL-2,4-DIAMINOPENTANE

[75] Inventors: Helmut Waldmann, Nideggen; Jürgen Dahmer, Krefeld, both of Germany; Anatoly Bazanov, St. Petersburg, Russian Federation; Alexandre Timofeev, St. Petersburg, Russian Federation; Natalja Zubritskaya, St. Petersburg, Russian Federation; Gennady Terechtchenko, St. Petersburg, Russian Federation

[73] Assignee: Bayer Aktiengesellschaft, Leverkusen, Germany

[21] Appl. No.: 961,675

[22] Filed: Oct. 31, 1997

[30] Foreign Application Priority Data

Nov. 5, 1996 [DE] Germany .................. 196 45 549.9

[51] Int. Cl.$^6$ .................................................. C07C 209/26
[52] U.S. Cl. .................. 564/472; 564/469; 564/470; 564/471
[58] Field of Search ................................ 564/469, 470, 564/471, 472

[56] References Cited

U.S. PATENT DOCUMENTS

| 3,904,625 | 9/1975 | Alink | 260/251 R |
| 4,652,625 | 3/1987 | Renken et al. | 528/123 |

FOREIGN PATENT DOCUMENTS 1276041  8/1968  Germany .

*Primary Examiner*—Brian M. Burn
*Attorney, Agent, or Firm*—Joseph C. Gil; Thomas W. Roy

[57] ABSTRACT

The present invention relates to a process for preparing 2-methyl-2,4-diaminopentane by introducing acetone, ammonia and hydrogen into a two-zone reactor at a temperature of 20° to 130° C. and a pressure of 30 to 250 bar, wherein the first zone contains a cationic exchange resin containing $NH_4^{\oplus}$ groups or an aluminum oxide and/or silicon oxide catalyst and the second zone contains a hydrogenation catalyst containing nickel.

4 Claims, No Drawings

PROCESS FOR THE PREPARATION OF 2-METHYL-2,4-DIAMINOPENTANE

BACKGROUND OF THE INVENTION

1. Field of the Invention

The present invention relates to a process for the preparation of 2-methyl-2,4-diaminopentane from 2,2,4,4,6-pentamethyl-2,3,4,5-tetrapyrimidine, ammonia and hydrogen.

2. Description of the Prior Art

U.S. Pat. 2,486,648 describes the preparation of 2-methyl-2,4-diaminopentane by the catalytic reduction of 2,2,4,4,6-pentamethyl-2,3,4,5-tetrahydropyrimidine with a mixture of hydrogen and ammonia. However, there are disadvantages to this process since under the reaction conditions, the pyrimidine derivative enters into unwanted secondary reactions at elevated temperatures in the presence of water.

An object of the present invention is to provide a process for the preparation of 2-methyl-2,4-diaminopentane in a higher yield. 2-methyl-2,4-diaminopentane is an important intermediate, for example, for raw materials for coating compositions.

This object may be achieved with the process according to the present invention described hereinafter.

SUMMARY OF THE INVENTION

The present invention relates to a process for preparing 2-methyl-2,4-diaminopentane by introducing acetone, ammonia and hydrogen into a two-zone reactor at a temperature of 20° to 150° C. and a pressure of 10 to 300 bar, wherein the first zone contains a cationic exchange resin containing $NH_4^{61}$ groups or an aluminum oxide and/or silicon oxide catalyst and the second zone contains a hydrogenation catalyst containing nickel.

DESCRIPTION OF THE INVENTION 2-methyl-2,4-diaminopentane is prepared from acetone, ammonia and hydrogen in accordance with the following scheme:

$$3\ CH_3-C-CH_3 \xrightarrow[-3H_2O]{+2NH_3}$$

[structure] $\xrightarrow[-C_3H_7NH_2]{+2H_2+NH_3}$ $CH_3-CH-CH_2-C(CH_3)_2$ with $NH_2$ and $NH_2$ groups In accordance with the present invention, it is possible to use acetone or compounds which yield acetone or are formed from acetone under the reaction conditions, for example, diacetone alcohol or acetone imines, such as acetone imine.

The reaction is performed at a temperature of 20° to 150° C., preferably of 50° to 130° C., and at a pressure of 10 to 300 bar, preferably of 30 to 250 bar.

The process according to the invention is performed in two zones. The catalyst in the first zone is selected from known sulphonated cationic exchange resins in the $NH_4^{61}$ form, and Al and/or Si oxides. In the second zone the catalyst is selected from catalysts containing 30 to 60 wt. % of nickel on chromium oxide. The catalyst may also contain copper.

In a preferred embodiment of the present invention, the starting materials (i.e., acetone or compounds which yield acetone under the reaction conditions, ammonia and hydrogen) are introduced into a first reaction zone, which contains sulphonated polystyrene resin in $NH_4^{61}$ form as the catalyst, and are then passed into a second zone which contains nickel on chromium oxide as catalyst, which has been reduced with hydrogen before the beginning of the reaction.

Once the mixture has passed through the reaction zones, the resulting product is worked up by distillation.

The invention is further illustrated but is not intended to be limited by the following examples in which all parts and percentages are by weight unless otherwise specified.

EXAMPLES

Example 1

The process was performed using two reactors, which contain fixed bed catalysts and are connected in series. The first reactor was charged with 200 cm³ of a sulphonated polystyrene cation exchange resin in $NH_4^{61}$ form (Ku-2-8) and the second reactor was charged with 500 cm³ of a reduced catalyst containing 48 wt. % of nickel on chromium oxide. Acetone was introduced at a flow rate of 50 ml/h and liquid ammonia was introduced at a flow rate of 20 ml/h into the bottom of the first reactor, wherein the temperature was maintained at 20° to 30° C. (room temperature) and the pressure was approx. 50 bar. Once the reaction mixture had passed through the first reactor, it was heated to 120° C. and introduced into the second reactor together with liquid ammonia (150 ml/h) and hydrogen (200 l/h). In the second reactor, the temperature was 120° C. and the pressure was 200 bar.

Once the mixture had passed through the second reactor, excess ammonia was removed from the reaction mixture by distillation. 41 g per hour of a product were obtained which contained 33.5 wt. % of 2-methyl-2,4-diaminopentane (yield: 65% of theoretical).

Example 2

The process was the same as in Example 1. The first reactor was charged with 200 cm³ of a catalyst which contained 17 wt. % of $Al_2O_3$ on silica gel as the catalyst. The second reactor was filled with 200 cm³ of a catalyst which contained 46 wt. % of nickel and 17 wt. % of copper on chromium oxide. The catalyst in the second reactor was reduced with hydrogen. Acetone and liquid ammonia were then each introduced at a rate of 10 ml/h into the bottom of the first reactor at a temperature of 90° C. and then into the second reactor at a temperature of 130° C. The pressure was 100 bar in both reactors.

Once the reaction mixture had passed through the first reactor, it was introduced into the second reactor together with ammonia at a rate of 30 ml/h and hydrogen at a rate of 100 l/h.

After the mixture had passed through the second reactor and the ammonia had been removed from the reaction mixture by distillation, a product containing 24.8 wt. % of 2-methyl-2,4-diaminopentane (48% of theoretical) was obtained at a rate of 12.2 g/h.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 2-methyl-2,4-diaminopentane which comprises introducing acetone, ammonia and hydrogen into a two-zone reactor at a temperature of 20° to 150° C. and a pressure of 10 to 300 bar, wherein the first zone contains a cationic exchange resin containing $NH_4^{61}$ groups or an aluminum oxide and/or silicon oxide catalyst and the second zone contains hydrogenation catalyst containing nickel.

2. The process of claim 1 wherein the reactor is maintained at temperature of 50° to 130° C.

3. The process of claim 1 wherein the reactor is maintained at a pressure of 30 to 250 bar.

4. The process of claim 2 wherein the reactor is maintained at a pressure of 30 to 250 bar.

* * * * *